United States Patent [19]

Lovelady

[11] 4,093,397
[45] June 6, 1978

[54] HIGH VACUUM PUMP

[76] Inventor: Grady R. Lovelady, 1624 San Altos Pl., Lemon Grove, Calif. 92045

[21] Appl. No.: 677,249

[22] Filed: Apr. 15, 1976

[51] Int. Cl.² ............................................. F04D 5/00
[52] U.S. Cl. .................................... 415/53 R; 55/320; 55/400; 55/467; 415/112; 417/424
[58] Field of Search ............... 32/33; 417/360, 423 R, 417/423 A, 430, 431, 424; 222/333, 383, 189, 145; 415/52, 111, 112, 175, 176, 121 G, 116, 206, 53 R; 15/353; 55/400, 319, 320, 467, 409; 210/416

[56] References Cited

U.S. PATENT DOCUMENTS

| | | | |
|---|---|---|---|
| 1,525,332 | 2/1925 | Sommer | 417/71 X |
| 2,102,353 | 12/1937 | Brock | 417/423 A |
| 2,114,780 | 4/1938 | Juelson | 417/423 A |
| 2,423,634 | 7/1947 | Berliner | 415/143 |
| 2,839,006 | 6/1958 | Mayo | 417/424 |
| 3,078,579 | 2/1963 | Jones et al. | 32/33 |
| 3,561,195 | 2/1971 | Bouru | 55/409 |
| 3,749,464 | 7/1973 | Satterthwaite | 415/112 |
| 3,802,807 | 4/1974 | Kilayko | 417/430 |
| 3,931,016 | 1/1976 | Lovelady | 55/400 X |

*Primary Examiner*—William L. Freeh
*Assistant Examiner*—Edward Look
*Attorney, Agent, or Firm*—Brown & Martin

[57] ABSTRACT

A high vacuum pump having a centrifugally filtered intake with a particular utility as an aspirator in a dentist's office, for example, having a coaxial intake/output at the pump's rotor hub with a radial outlet therefrom, a liquid pressure seal on the top and bottom of the pump impeller assembly and an automatically flushed sump tank surrounding the intake filter.

7 Claims, 7 Drawing Figures

4,093,397

HIGH VACUUM PUMP

BRIEF DESCRIPTION OF THE INVENTION

The present invention relates to a high vacuum pump and, more particularly, to a high-vacuum pump having a centrifugally filtered intake.

According to the invention, a high vacuum pump is provided in which an operating inlet enters the top of a sump tank. The pump has a coaxial intake at its rotor hub terminating in a mesh filter screen projecting downwardly from the central intake port into an input sump tank. The input sump tank is filled with water up to the bottom of the filter screen so when the level from an intake liquid raises above the screen, water and air is pulled through the rotating screen upwardly into the pump and outwardly radially from the pump. Another novel feature, which appears to give the pump over double the normally expected vacuum, lies in the liquid pressure seal on the top and bottom of the impeller assembly.

During a period when the pump is not in use, such as in the evening in the case of an installation in a dentist's office, for example, a timer opens the solenoid actuated valve which supplies flushing water to the sump tank, raising the level to a drain level which then drains out the top layer of water where floating debris has a tendency to collect. Periodically, the sump tank is removed, emptied, flushed, and replaced. One of the main purposes of the assembly is the elimination of mercury in sewage which is becoming of increasing concern.

An object of the present invention is the provision of a highly efficient high vacuum pump.

Another object of the invention is the provision of a high vacuum pump having a centrifugally filtered intake.

A further object of the invention is the provision of a high vacuum pump with a radial outlet.

Yet another object of the invention is the provision of a high vacuum pump for utilization with an aspirator.

Other objects and many of the attendant advantages of the present invention will be readily appreciated as the same becomes better understood by reference to the following detailed description when considered in connection with the accompanying drawings in which like reference numerals designate like parts throughout the Figures thereon and wherein.

DETAILED DESCRIPTION OF THE INVENTION

Figure 1:
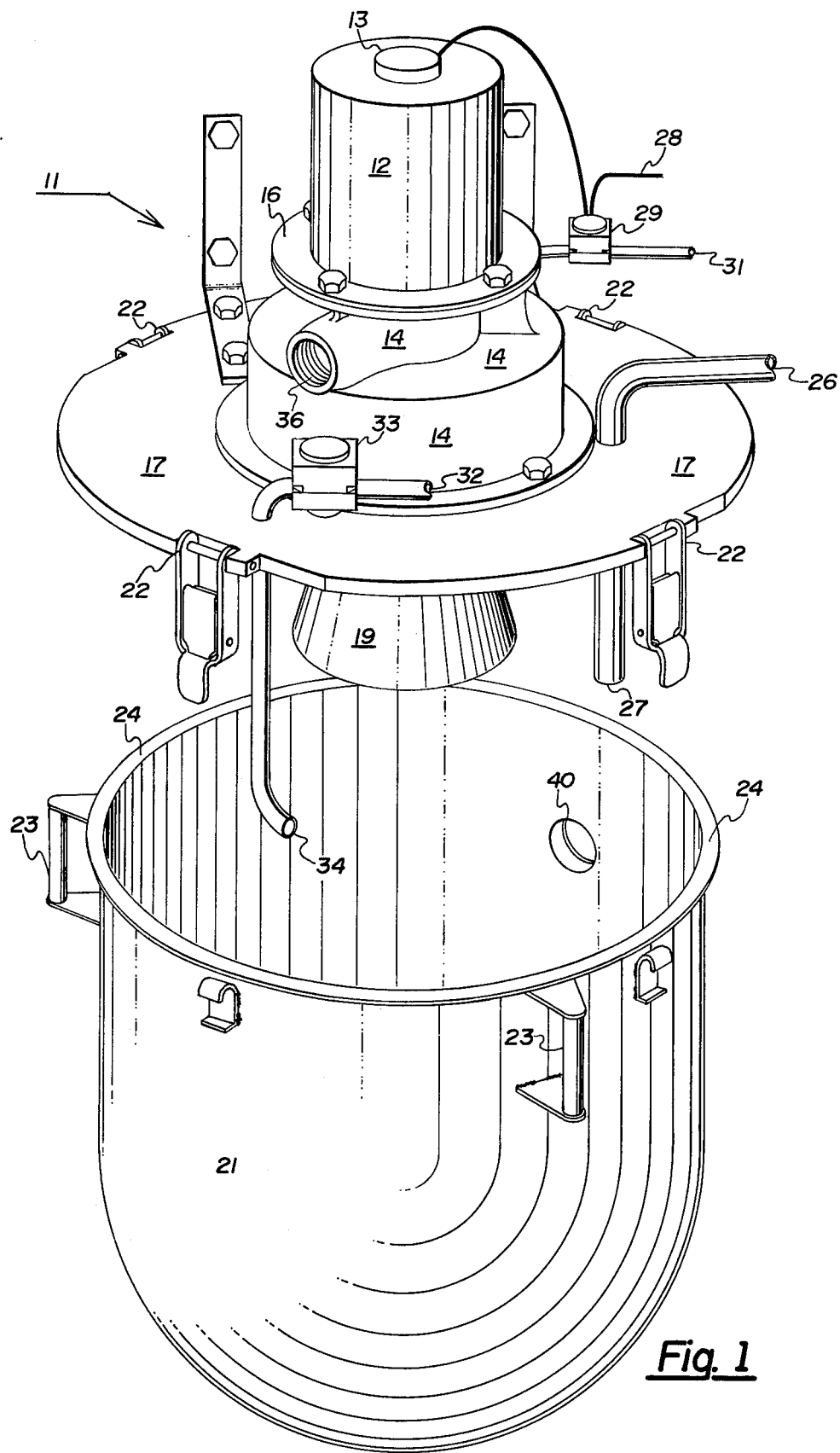
FIG. 1 is an exploded view in perspective of the preferred embodiment of the present invention.

Referring to FIG. 1, the pump assembly of the present invention is shown generally at 11 having a motor 12 with a shaft 12A (not shown) projecting into pump housing 14. Motor 12 is carried by pump housing 14 via motor flange 16. Pump housing 14 is carried by main mounting plate 17 and has a shaft (not shown) carrying a cylindrical filter screen 18 (not shown) projecting downwardly therefrom and surrounded by a cone 19. Sump tank 21 is removably coupled to main mounting plate 17 via clamps 22. Sump tank 21 also has handles 23 and terminates in its upper portion at a sealing flange 24. An operating inlet 26 empties into sump tank 21 at 27. Electrical leads 28 are coupled to solenoid valve 29 and motor 12. Cooling and sealing inlet 31 is coupled through solenoid valve 29 into pump housing 14. A flushing inlet 32 is coupled through solenoid valve 33 and into sump tank 21 at 34. Main drain outlet 36 is coupled from pump housing 14. Sump tank 21 has a flush drain 40.

Figure 2:
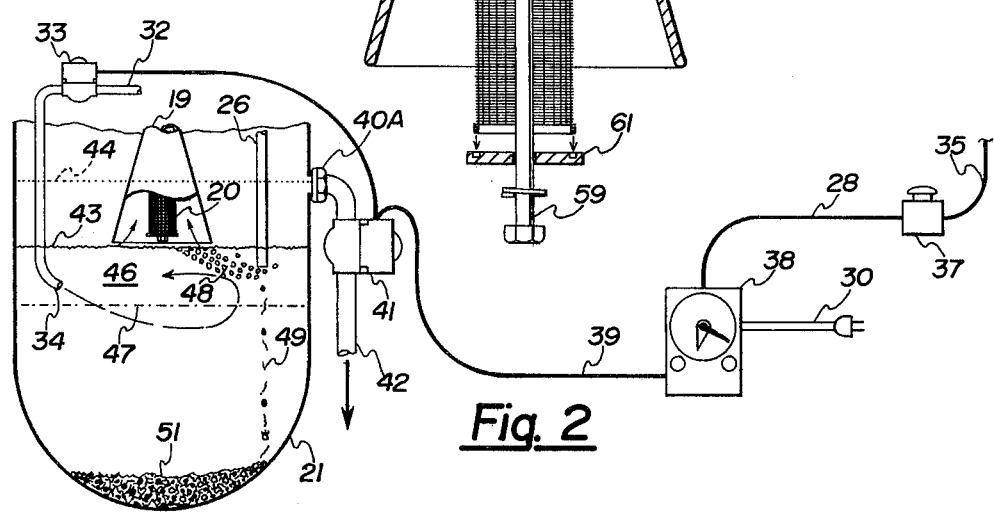
FIG. 2 illustrates the electrical system of the embodiment of FIG. 1.

Referring to FIG. 2, input electrical leads 35 are coupled through switch 37 to timer 38. Timer 38 couples power through leads 39 to solenoid-actuated valves 41 and 33. Solenoid actuated valve 41 is in exhaust line 42 of sump tank 21. Sump tank 21 is shown filled with water to operating level 43. Flushing level 44 is shown in dotted lines and debris zone 46 is indicated between operating level 43 and dotted line 47. Operating inlet line 26 is shown having air bubbles 48 moving toward cylindrical filter drum 20 with heavy debris 49 collecting in the bottom of sump tank 21 at 51.

Figure 3:
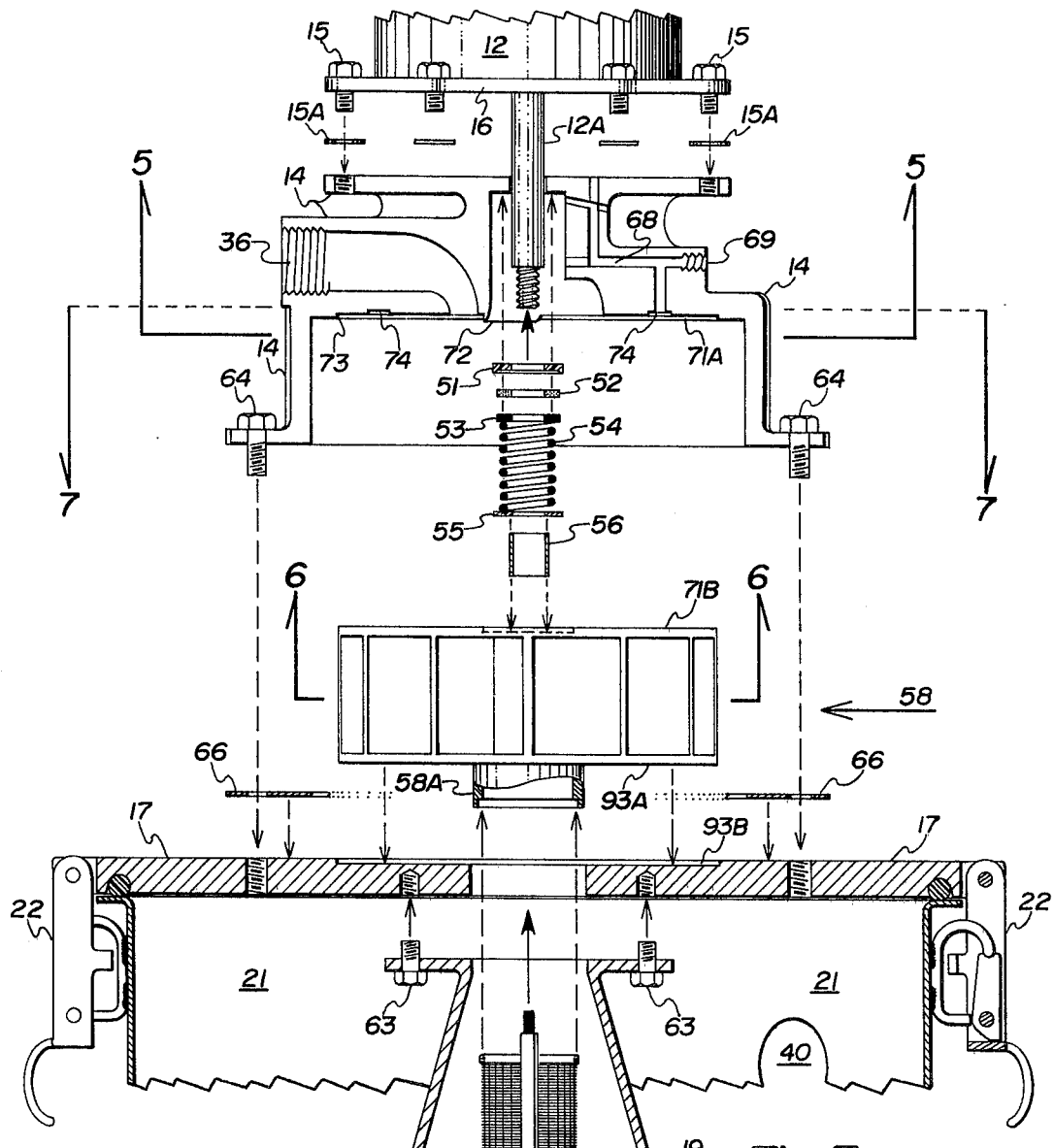
FIG. 3 is a vertical exploded view partially sectioned of the embodiment of FIG. 1.

Referring to FIG. 3, motor 12 is carried by motor flange 16 which is coupled via threaded bolts 15 to pump housing 14. Shims 15A assure proper spacing. Motor shaft 12A is threadably coupled to the pump hub (not shown) and passes through elastomeric seal washer 51, static ceramic thrust washer 52, rotating graphic washer 53, compression spring 54, washer 55, and sleeve 56, which abuts the pump hub 58A. Impeller assembly 58 is carried by hub 58A which in turn carries filter screen cylinder 20 via threaded shaft 59 which mounts end plate 61 to the bottom of filter cylinder 20. Deflector cone 19 is mounted via threaded bolts 63 to main mounting plate 17. Pump housing 14 is mounted to main mounting plate 17 via threaded bolts 64 which pass through shims 66 for proper spacing thereof. Cooling vent 68 is in communication with rotating graphite washer 52 and static ceramic thrust washer 51 on one end via chamber 60 (FIG. 4) and with the sealing water input 69 at another end. Sealing gap 71, formed by recess 71A in pump housing 14 and top impeller plate 71B, is also in communication with sealing water input port 69. Recess 74 forms an annular water sealing groove in communication with inlet 69. A lower water seal gap 93 is formed between bottom impeller plate 93A and recess 93B in main mounting plate 17.

Figure 4:
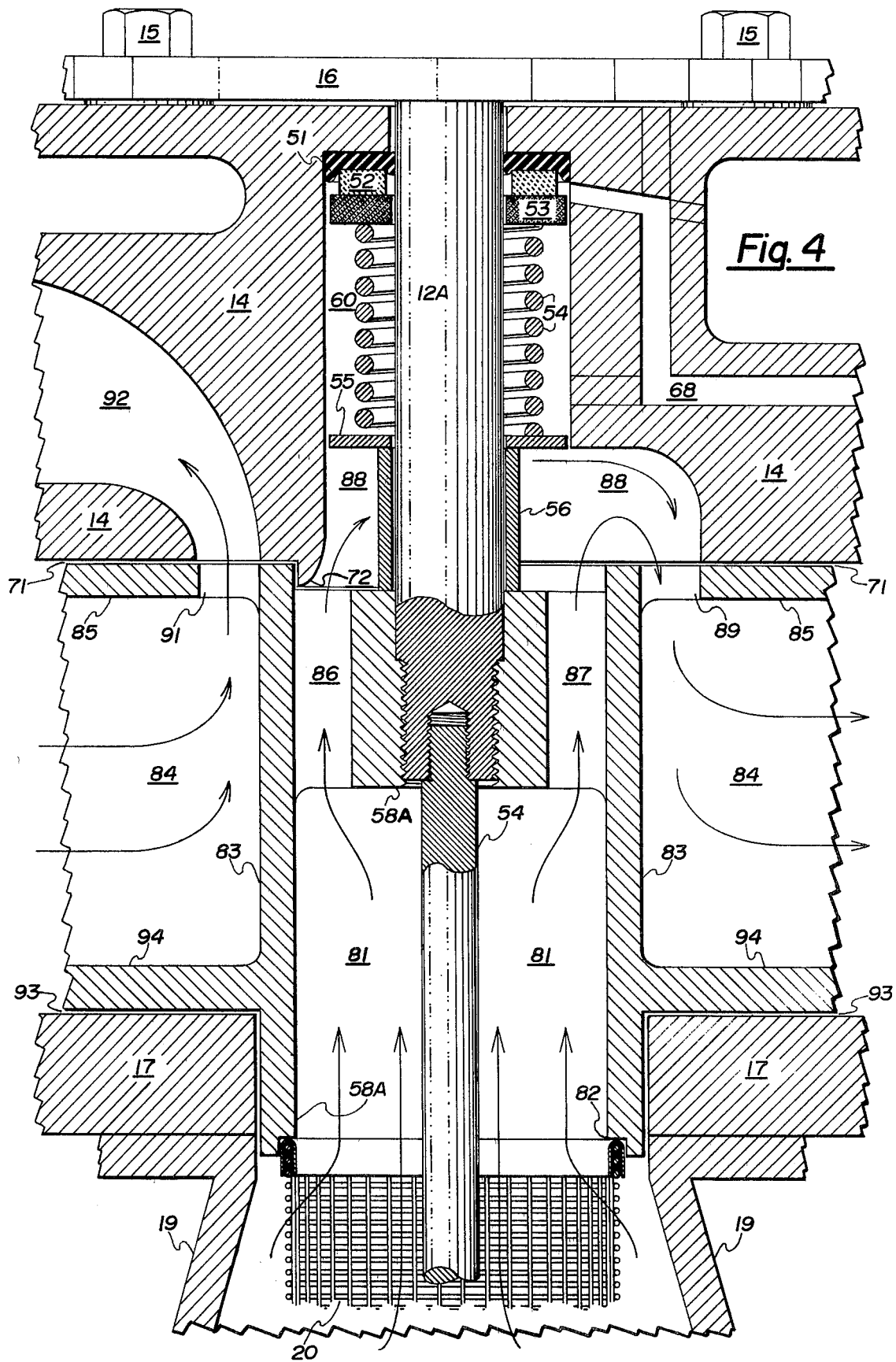
FIG. 4 is an assembled sectional view of the central portion of FIG. 3.

Referring to FIG. 4, motor flange 16 is shown carried by pump housing 14 with motor shaft 17A projecting downwardly and in threadable engagement with hub 58A. Hub 58A is in threadable engagement with filter shaft 59 which passes through first intake chamber 81 disposed above cylindrical filter screen 20. Cylindrical filter screen 20 is held in screen mounting groove 82 in impeller core 83. Impeller vanes 84 are carried by impeller core 83. First input chamber 81 is in communication with inlet ports 86 and 87, which in turn, are in communication with second intake chamber 88. Second intake chamber 88 is in communication with inlet/outlet port 89. Inlet/outlet port 91 is in communication with impeller vane 84 and outlet chamber 92. Motor shaft 12A carries sleeve 56, washer 55, rotating graphite washer 53, static ceramic thrust washer 52 and elastomeric seal washer 51. Compression spring 54 is compressed between rotating graphite washer 53 and washer 55. Water channel 68 is in communication with static ceramic thrust washer 52 and elastomeric seal washer 51 and rotating graphite washer 53. Water seal gap 71 is in communication with water channel 68 (FIG. 3). Water seal gap 93 receives water from centrifically thrown water from impeller blades 84.

Figure 5:
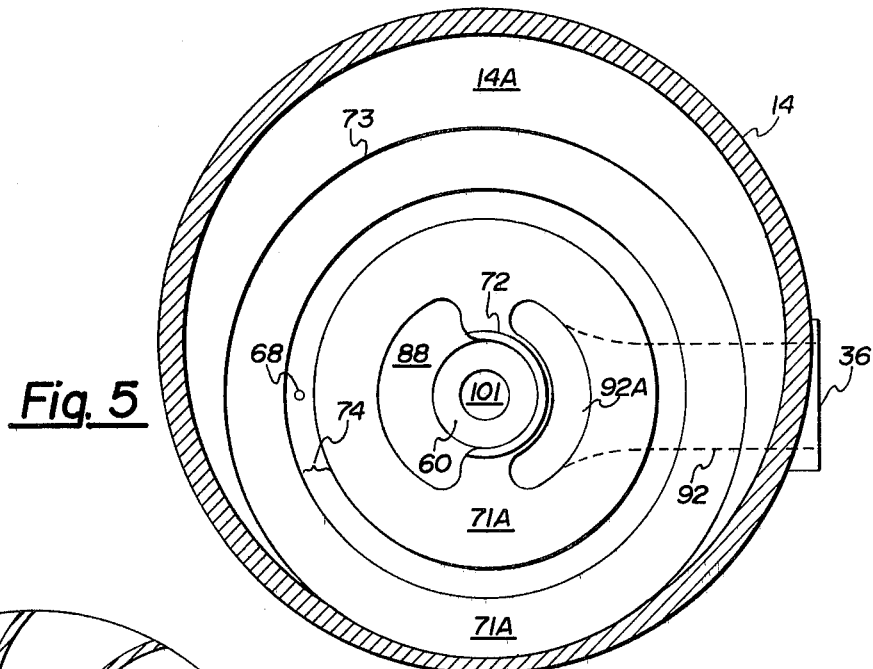
FIG. 5 is a sectional view taken along lines 5—5 of FIG. 3.

Referring to FIG. 5, a lower and sectional view as taken and indicated on FIG. 3 is shown with the housing 14 cross hatched and a new feature being first visible, this feature being the transfer chamber 14A into which the gas liquid pumped medium can be transferred from the input section and from which it is taken by the output action of the impeller 58. The impeller 58 lies within a declivity 71A (FIG. 3) outlined by recess shoulder 73 (also see FIG. 3) and the flat surface of that declivity forms the upper boundary 71A of water seal gap 71 previously indicated. A further declivity 74 constitutes an annular water groove existing within that surface, this water groove 74 is supplied with sealing water via channel 68. Centrally located within FIG. 5 is a shaft bore 101 surrounded by the sealing component cavity 60 and contiguous in its near extremity with the second intake chamber 88. On the opposite side of cavity 60 is the mouth of the outlet chamber 92A deeper in the casting 14, the casting being the pump housing 14, communicates through an outlet chamber 92 indicated by dash lines and communicates with the main drain outlet 36.

Figure 6:
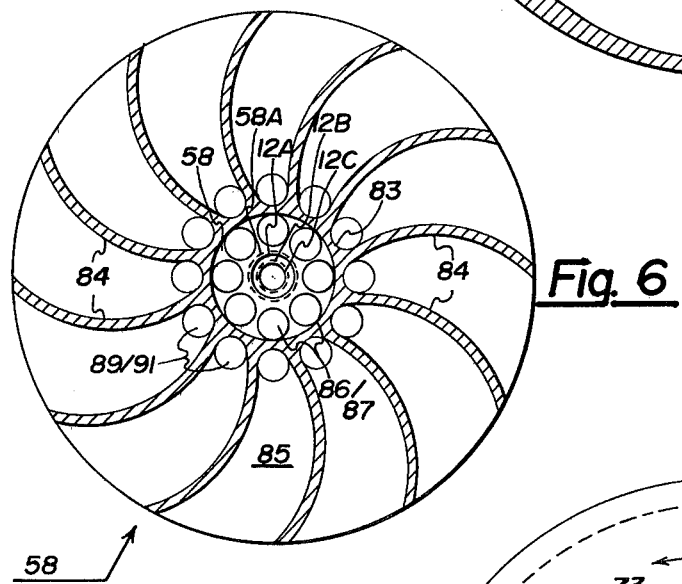
FIG. 6 is a sectional view taken along lines 6—6 of FIG. 3.

Referring now to FIG. 6, wherein the impeller 58 is depicted in cross section along lines 6—6 shown on FIG. 3. A central clearance bore for the filter bolt is designated at 12C. This is surrounded by threads for the filter bolt designated at 12B and are an integral portion of the motor shaft 12A which is surrounded by threads to receive the hub 58A which also contains inlet/outlet ports 86/87, the number depending on the area in which the flow from these ports impinges. Flow from inlet ports impinges on the deflector ridge 72 visible in FIGS. 4 and 5, and flow inlet from ports 87, impinges on the open second intake chamber 88. The core of the impeller is indicated 83 and is surrounded by inlet/outlet ports 89/91. The function of these ports and the number ascribed to them depends upon their location within the operating unit at any given time. Between the multiplicity of input/output ports 89/91 lie a multiplicity of curved vanes 84.

Figure 7:
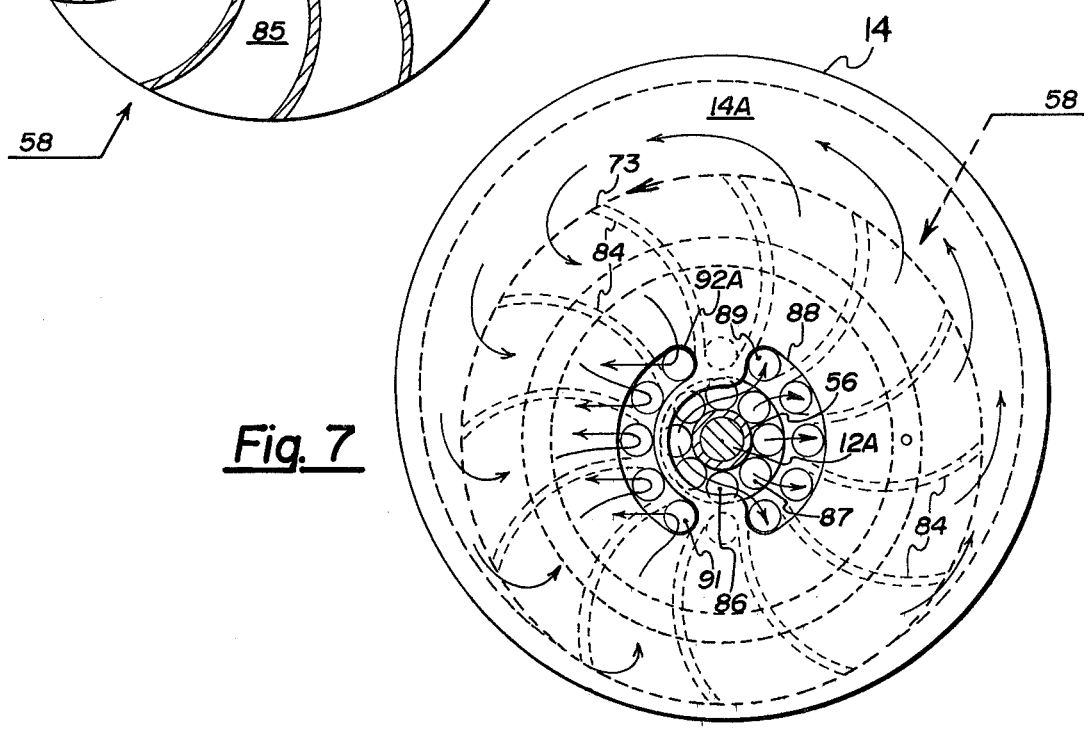
FIG. 7 is a phantom sectional view through the pump housing along lines 7—7 of FIG. 3 with cross hatching deleted for clarity.

FIG. 7 represents a phantom section of the pump housing 14 looking down along the section lines 7—7 indicated in FIG. 3. Cross hatching of the pump housing 14 has been omitted so that the interrelation between that housing 14 and the impeller 58 may be viewed. In a center location is the motor shaft 12A surrounded by sleeve 56. These are immediately surrounded by inlet ports 86 on the top, bottom, and left side where the upward flow through the intake ports 86 impinges on the deflector ridge 72, and they are surrounded on the right side by inlet ports 87 where the upward flow freely enters into inlet chamber 88. Flow from all of the inlet ports 86 and 87 either comes around the sleeve 56 or flows directly into inlet/outlet ports 89 at the top of the impeller and viewable through the inlet chamber opening 88. The rising pump media is therefore transferred radially to the ports between vanes 84 throughout almost the entire right half of FIG. 7. Solid arrows of flow indicate that this pumped media now flows from between the vanes 84 and enters a transfer chamber 14A which becomes increasingly larger in the direction of impeller rotation which is in this view counterclockwise. On the left side of the figure, arrows indicate the pump media entering inbetween vanes 84 and traveling inward toward the impeller core 83 (see FIG. 6). From whence that pumped media flows upward through inlet/output ports 91 and into the mount of outlet chamber 92A from which it passes into the outlet chamber 92 (see FIG. 4) and out the main drain outlet 36 (see FIG. 3).

The invention claimed is:

1. A high vacuum pump comprising:
    a generally cylindrical housing having a housing inlet and a housing outlet,
    an impeller assembly having a rotor hub in the center thereof rotatably mounted eccentrically of the axis of said housing, said hub defining a passageway extending the length thereof and forming an intake at one axial end thereof;
    an outlet at the other axial end of said hub, said outlet communicating via an inlet chamber in said housing with impeller blades in said impeller assembly on one radial side thereof; and
    an exhaust duct on the other radial side of said impeller assembly extending radially from the axis of said rotor hub.

2. The high vacuum pump of claim 1, wherein said impeller assembly is at a generally cylindrical configuration having opposite generally circular end surfaces,
    first and second water seals between the housing and the circular surfaces, respectively, of said impeller assembly.

3. The high vacuum pump assembly of claim 1, wherein:
    said housing outlet communicates with said impeller radially from the outer diameter thereof closely adjacent the axis thereof.

4. The high vacuum pump of claim 1 and further including:
    centrifically filtered intake means at said hub inlet.

5. The high vacuum pump of claim 4 and further including:
    a sump tank surrounding said centrifically filtered intake means.

6. The high vacuum pump of claim 4 and further including:
    automatic flushing means coupled to said sump tank.

7. The high vacuum pump of claim 4, wherein:
    said filter comprises a cylindrical filter element mounted on the end of and extending co-axially of said hub, and
    an open ended cone surrounding said filter element.

* * * * *